United States Patent [19]

Blank et al.

[11] Patent Number: 5,714,647
[45] Date of Patent: Feb. 3, 1998

[54] PROCESS FOR THE ADIABATIC PREPARATION OF MONONITROHALOGENOBENZENES

[75] Inventors: Heinz Ulrich Blank, Odenthal-Glöbusch; Helmut Judat, Langenfeld; Bernd-Michael König, Bergisch Gladbach, all of Germany

[73] Assignee: Bayer Aktiengesellschaft, Leverkusen, Germany

[21] Appl. No.: 785,577

[22] Filed: Jan. 21, 1997

Related U.S. Application Data

[63] Continuation of Ser. No. 409,112, Mar. 23, 1995, abandoned.

[30] Foreign Application Priority Data

Mar. 30, 1994 [DE] Germany ............... 44 11 0064.2

[51] Int. Cl.⁶ ............................................. C07C 205/00
[52] U.S. Cl. .................................. 568/937; 568/938
[58] Field of Search ............................ 568/937, 938

[56] References Cited

U.S. PATENT DOCUMENTS

| | | | |
|---|---|---|---|
| 1,586,253 | 5/1926 | Livingston et al. ................ | 568/937 |
| 2,256,999 | 9/1941 | Castner ............................... | 260/645 |
| 3,928,476 | 12/1975 | Shimada et al. .................... | 260/646 |
| 4,021,498 | 5/1977 | Alexanderson et al. ............ | 260/645 |
| 4,091,042 | 5/1978 | Alexanderson et al. ............ | 260/645 |
| 4,339,618 | 7/1982 | Rosner ............................... | 568/937 |
| 4,420,645 | 12/1983 | Vaidyanathan .................... | 568/937 |
| 4,453,027 | 6/1984 | Vaidyanathan .................... | 568/937 |
| 4,973,770 | 11/1990 | Evans ................................. | 568/929 |
| 5,313,009 | 5/1994 | Guenkel et al. .................... | 568/927 |

FOREIGN PATENT DOCUMENTS

| | | |
|---|---|---|
| 0436443 | 7/1991 | European Pat. Off. . |
| 0551144 | 7/1993 | European Pat. Off. . |

*Primary Examiner*—Paul J. Killos
*Attorney, Agent, or Firm*—Sprung Kramer Schaefer & Briscoe

[57] ABSTRACT

Mononitrohalogenobenzenes can be prepared by mixing halogenobenzene, nitric acid, sulphuric acid and water intensively with one another, simultaneously or in succession in their total quantity, and by redispersing them at least twice in the case of continuous preparation, applying a mixing energy of 1–40 watts per liter of the overall reaction mixture, preferably 3–30 W/l, largely suppressing back-mixing in the continuous procedure, and observing adiabatic reaction conditions.

20 Claims, No Drawings

PROCESS FOR THE ADIABATIC PREPARATION OF MONONITROHALOGENOBENZENES

This application is a continuation, of application Ser. No. 08/409,112, filed on Mar. 23, 1995 which is abandoned.

BACKGROUND OF THE INVENTION

1. Field of the Invention

The present invention relates to the preparation of mononitrohalogenobenzenes by a highly selective process which is free from waste acid and utilizes the heat of reaction.

Mononitrohalogenobenzenes are important intermediates for the production of plastics, dyes and auxiliaries.

2. Description of the Related Art

Mononitrohalogenobenzenes are prepared industrially by isothermic nitration of halogenobenzenes at relatively low temperatures (from 60° to 90° C.). In this procedure large quantities of contaminated waste acid are obtained which have to be disposed of or worked up in a cost-intensive operation. A disadvantage of this process is that a considerable heat of reaction has to be removed, and this energy is obtained at a low level so that it cannot be utilized.

A further disadvantage is that additional energy must be employed in order to concentrate the cold spent acid. In addition, the separation of organic and inorganic phases after the nitration presents difficulties. Residual organic material must be removed from the spent acid by extraction.

In order to avoid the production of waste acid, processes must be sought which comprise an integrated sulphuric acid concentration operation with utilization of the heat of reaction. This necessitates a circulating acid in which by-products may not accumulate and use of high reaction temperatures, in order to be able to concentrate the sulphuric acid in an industrially cost-effective manner.

The adiabatic mononitration of benzene is described in a series of patent documents (U.S. Pat. Nos. 2,256,999, 4,021,498, 4,091,042, 4,973,770, EP 436 443). The above-mentioned energetic disadvantages in the isothermal nitration of halogenobenzenes do not occur in the adiabatic nitration of benzene, since the heat of reaction thereof is obtained at a high level (temperature of the spent acid >100° C.) and can be used to concentrate the acid. Although the extension of this procedure to the mononitration of halogenobenzenes is mentioned in U.S. Pat. Nos. 2,256,999, 4,021,498, 4,973,770 and EP 436 443, in none of these has it been described in an Example. It must therefore be assumed that the adiabatic nitration of aromatic compounds other than benzene in accordance with these patent documents is purely speculative in nature. The temperature of 100° C. according to U.S. Pat. No. 4,973,770, for example, is above that known from the isothermal nitration of halogenobenzenes (see above).

In the process described in U.S. Pat. No. 4,973,770, there is furthermore a single atomization and fine distribution of the benzene which is intended to help control the overall course of the reaction. In order to maintain the fine distribution for as long as possible, the coalescence of the atomized particles with one another and with the wall must be avoided; to avoid wall contact, a reactor having a large diameter compared with the nozzle diameter is employed, which permits a high degree of back-mixing: according to the exemplary embodiment of U.S. Pat. No. 4,973,770 in conjunction with FIG. 1, benzene is passed through a spray nozzle having a diameter of 0.5 mm into a reactor having a diameter of 75 mm. With an overall reactor length of 430 mm, the mixed acid is added at a distance of 150 mm from the nozzle, where the energy of the nozzle jet is already substantially consumed for the back-mixing. The mixing of the added mixed acid with the benzene sprayed in takes place at a low energy level and with a lesser intensity.

The claim of EP 436 443, according to which mixed acids containing nitronium ions are used which have molar compositions as given by FIG. 6 in EP 436 443, is also outside that which is familiar to those skilled in the art. Thus the point D highlighted in FIG. 6, in conjunction with p. 9, lines 10 to 12 of EP 436 443, indicates an acid whose composition is 72.02 mol % $H_2SO_4$, 2.99 mol % $HNO_3$ and 24.99 mol % $H_2O$, corresponding to 91.71% by weight of $H_2SO_4$, 2.45% by weight of $HNO_3$ and 5.84% by weight of $H_2O$. An acid of this strength is not suitable for an industrial, economic process for the adiabatic preparation of mononitrohalogenobenzenes. Furthermore, circulation of the waste acid produced in this process is not industrially justifiable, since the degree of concentration required, to far more than 90% by weight, is too expensive. This process is therefore not economically rational and is unable to provide those skilled in the art with information on achieving the present object.

An adiabatic nitration process for the preparation of mononitrohalogenobenzenes is claimed in U.S. 4,453,027. The conditions described therein, however, are unsuitable for a rational industrial implementation. The nitrating acid used contains 11.2% by weight $HNO_3$, 68.5% by weight $H_2SO_4$ and 20.3% by weight $H_2O$. A temperature of from 100° to 110° C. is given for the outflowing spent acid. In the case of adiabatic implementation, however, the temperature increase during the reaction is about 100° C. at such an $HNO_3$ concentration, so that it is necessary to commence the reaction at from 0° to 10° C. and for the reactants to be employed to be available at this temperature. The outflowing spent acid (waste acid) must be concentrated to 84.1% by weight of $H_2SO_4$ if 60% strength $HNO_3$ is used, and to 77.3% by weight $H_2SO_4$ even if 98% strength $HNO_3$ is used. If the heat of reaction is used for this purpose, the waste acid is cooled to about 0° C. in the process. Such a process is no longer industrially and economically rational, since it necessitates use of cooling sols and special apparatus.

However, halogenobenzenes can be mononitrated adiabatically at high reaction temperatures and with high selectivity by employing the steps and conditions described below.

SUMMARY OF THE INVENTION

The invention relates to a process for the continuous or batchwise preparation of mononitrohalogenobenzenes by reaction of halogenobenzenes with an $HNO_3/H_2SO_4/H_2O$ mixture with formation, essentially, of the mononitrohalogenobenzenes and water of reaction, characterized by the steps of a) feeding the reactants halogenobenzene, $HNO_3$, $H_2SO_4$ and $H_2O$ in any sequence into a reactor equipped with mixing elements, a1) the quantity of $HNO_3$ is from 1 to 8% by weight, the quantity of $H_2SO_4$ is from 56.5 to 84.5% by weight and the quantity of $H_2O$ is the remainder to 100% by weight, and 100% by weight represents the sum of $HNO_3+H_2SO_4+H_2O$, a2) the $H_2O$ is employed as such, as dilution $H_2O$ of the $HNO_3$, as dilution $H_2O$ of the $H_2SO_4$ or in a plurality of the forms mentioned, and a3) the molar ratio of halogenobenzene to $HNO_3$ is from 0.9 to 1.5, b) rapid and intensive mixing of the total quantity of the reactants, for which a mixing energy is employed of from 1 to 40 watts per liter of the overall reaction mixture, preferably from 3 to 30 w/l, c) carrying out the reaction under adiabatic conditions, the reactants being fed in at temperatures such that the mixing takes place in the range from 60° to 160° C. and the temperature at the end of the reaction does not exceed 180° C., d) separating the reaction mixture, after carrying out the reaction, into an organic and an inorganic phase, and e) working up the substantially $HNO_3$-free inorganic phase by distillation with removal of water.

DETAILED DESCRIPTION OF THE INVENTION

Halogenobenzenes in the context of the invention are chlorobenzene, o-, m-, p-dichlorobenzene, o-, m-, p-chlorotoluene and bromobenzene, preferably chlorobenzene and o-, m-, p-dichlorobenzene, particular preference being given to chlorobenzene and o-dichlorobenzene.

The process according to the invention can be carried out continuously or batchwise, preferably continuously.

The continuous procedure can be carried out, for example, as follows: the total quantity of the reactants is rapidly mixed with the aid of the mixing elements and are fed as a mixture into a reactor. The mixing time for the continuous procedure is generally less than 3 sec, for example from 1 msec to 2.99 sec, preferably from 1 msec to 2 sec. The reactor is insulated if desired, substantially prevents back-mixing and is operated adiabatically. For the substantial prevention of back-mixing, the reactor is subdivided or is composed of a plurality of chambers or units; at the transitions between the reactor parts, the reaction mixture is redispersed. After full reaction the mixture flows out and is separated in a separation vessel; the separation occurs rapidly. The organic phase is worked up in the usual manner, for example by washing and distillation, or is fed immediately to a second nitration. In general, especially when there is an excess of halogenobenzene, the inorganic phase separated off is virtually free of nitric acid. Should this not be the case, especially when there is an excess of nitric acid, residual nitric acid can be consumed in a downstream reactor with addition of further halogenobenzene in the manner of a reactive extraction. The inorganic acid phase, substantially freed of nitric acid, is preferably fed to a flash evaporation with utilization of the heat of reaction absorbed and under reduced pressure. In this operation water is removed from the acid and the acid is preferably and simultaneously brought to the initial concentration and the initial temperature for step a). This recycling of the worked-up inorganic phase ($H_2SO_4$, $H_2O$) to the process results in a circulation procedure for the $H_2SO_4$; it may be expedient to expel a small proportion of this $H_2SO_4$ in order to reduce any contamination to a low level. In the event that the inorganic phase still contains halogenobenzene, nitrohalogenobenzene and any organic by-products, it may be expedient to strip the inorganic phase prior to the flash evaporation in order to remove the organic components. The water obtained subsequently as flash condensate is then of relatively high purity, and is easier to dispose of. Of course, the flash condensate can also be freed from organic components by stripping, to leave, similarly, a residual flash condensate of relatively high purity. The organic compounds obtained in the downstream reaction of the $HNO_3$ with further halogenobenzene and in the stripping operation can be added to the process at a suitable point (halogenobenzene, (di) nitrohalogenobenzene) or are expelled and disposed of (contaminants, by-products).

The reactants can be fed together or else individually or as mixtures of two or three thereof, simultaneously or in succession, to the reactor equipped with mixing elements. The feedstocks can be mixed, for example, in such a way that halogenobenzene and nitric acid are added to the concentrated, spent sulphuric acid, simultaneously or in succession, as two separate streams, in which case the nitric acid may be diluted by water and/or sulphuric acid and water. The halogenobenzene can also be premixed with water and sulphuric acid and the resulting emulsion can be mixed further, rapidly and intensively, with nitric acid, which may be mixed with sulphuric acid and/or water. Furthermore, the halogenobenzene can also be intensively mixed with a mixed acid comprising $H_2SO_4$, $HNO_3$ and $H_2O$. Those skilled in the art will be readily able to detect still more variants for feeding the reactants, for their intensive mixing and for the subsequent treatment according to the invention. The mixing elements known in the art are suitable for this purpose, for example: 1. static mixers, 2. pumps, 3. nozzles, 4. agitators or combinations thereof.

The sequence and combination of mixing the reactants nitric acid and halogenobenzenes and also sulphuric acid and water with one another is of little importance for the success of the reaction, provided the reaction mixture has the composition according to the invention after the overall mixing, and the mixing takes place at the intensity according to the invention and, when the reaction is carried out continuously, substantially free from back-mixing.

The intensity of mixing in the batchwise procedure, apart from the high energy input, can also be characterized by the short time for addition of the reactants, which amounts to 0.001–15%, preferably 0.001–3%, of the time required for the reaction between the halogenobenzene and $HNO_3$ to occur. Consequently it is also possible to carry out the process according to the invention batchwise in a stirred reactor.

The feeding and intensive mixing of the reactants are followed, in the continuous procedure, by at least two dispersion operations. For this purpose the reactor contains perforated metal sheets, slotted metal sheets, impact baffles, agitators or similar internals and/or elements which are known for this purpose to those skilled in the art.

Continuously operated reactors for the process according to the invention which may be mentioned by way of example are: tubular reactors having internals for redispersion, such as flow breakers, deflection baffles, static mixers, agitators and the like; vigorously stirred reactors in a cascade arrangement; loop reactors having internals as above; combinations of a plurality of the apparatus mentioned; other reactors of equivalent action, such as chamber reactors with agitators in each chamber. Tubular reactors having internals are preferably employed. The internals are preferably perforated metal sheets. All internals represent subdivisions of the overall apparatus, which serve equally for the redispersion and for the substantial prevention of back-mixing.

After the intensive mixing, after each dispersion and after the mixture has flowed through a certain part-length of the reactor, coalescence of the dispersion droplets is observed, which can be reversed by redispersion. The number of dispersion operations is, according to the invention, 2–50, preferably 3–30, particularly preferably 4–20. In order to overcome the pressure losses which occur in these operations, a mixing energy, per liter of the overall reaction mixture, of 1–40 watts/liter, preferably 3–30 W/l, is input into the reaction system with the reactants.

The reactants are mixed in the range from 60° to 160° C., preferably from 70° to 140° C. and particularly preferably from 80° to 120° C. Adiabatic reaction conditions are maintained. The final temperature depends on the value of the mixing temperature, on the proportions of the reactants and on the conversion; it does not exceed 180° C. in general and 160° C. in most cases.

The content of added nitric acid in the reaction mixture at the time of mixing, relative to the sum of nitric acid, sulphuric acid and water, is from 1 to 8% by weight, preferably from 2 to 6% by weight and particularly preferably from 2.5 to 5% by weight. Nitric acid can be used in highly concentrated form or in azeotropically boiling form, for example as 60–98% strength $HNO_3$, but preferably in the form of the cheaply available "weak acid", having a strength of approximately 60–65% by weight.

The content of sulphuric acid in the reaction mixture at the time of mixing, relative to the sum of nitric acid, sulphuric acid and water, is from 56.5 to 84.5% by weight, preferably from 65 to 79% by weight and particularly preferably from 67.5 to 77% by weight.

The remainder to 100% by weight is $H_2O$. This can be employed as such, as dilution $H_2O$ of the $H_2SO_4$, as dilution $H_2O$ of the $HNO_3$ or in a plurality of the forms mentioned. In its preferred form, $H_2O$ is present as dilution $H_2O$ of both the $H_2SO_4$ and the $HNO_3$.

Since the intensity of nitration, with changing contents of nitric acid in the nitration acid, is dependent on the ratio of sulphuric acid to water, it is determined and, if desired, is adjusted on the basis of the sulphuric acid concentration of the outflowing and substantially nitric acid-free spent acid. This $H_2SO_4$ concentration of the spent acid is intended in accordance with the invention to be from 60 to 85% by weight, preferably from 68 to 80% by weight and particularly preferably from 70 to 78% by weight. For reuse, the outflowing sulphuric acid is concentrated by from 0.6 to 7.5 percentage points, in many cases by from 1.7 to 4.2 percentage points, with the distillative expulsion of water (water of reaction, possibly dilution water). For this purpose the heat of reaction absorbed from the outflowing $H_2SO_4$ is preferably utilized and a reduced pressure of from about 40 to 150 mbar, preferably from 40 to 120 mbar and particularly preferably from 50 to 100 mbar, is employed. This can be carried out, for example, in the form of a flash evaporation. The $H_2SO_4$ obtained thereby is suitable for use in step a). The distillative expulsion of water is preferably carried out such that the temperature and concentration of the concentrated $H_2SO_4$ correspond directly to the values required in step a). Such a utilization of the heat of reaction renders the process according to the invention more economical than the known processes for the preparation of nitrohalogenobenzenes.

Possible embodiments with respect to the mixed acids having varying compositions, to the outflowing $H_2SO_4$ concentration, to the temperature conditions and to the pressure of the flash evaporation and degree of concentration of the $H_2SO_4$ may be summarized by way of example as follows (cases a and c: chlorobenzene; case b: o-dichlorobenzene):

| Mixed acid | a | b | c |
|---|---|---|---|
| $HNO_3$ (% by wt.) | 3.00 | 3.00 | 5.00 |
| $H_2SO_4$ (% by wt.) | 68.50 | 74.37 | 67.50 |
| $H_2O$ (% by wt.) | 28.50 | 22.63 | 27.50 |
| Strength of the acids employed | | | |
| $HNO_3$ (% by wt.) | 60.00 | 60.00 | 60.00 |
| $H_2SO_4$ (% by wt.) | 72.11 | 78.28 | 73.64 |
| outflowing $H_2SO_4$ (% by wt.) | 70.00 | 76.00 | 70.00 |
| Mixing temperature (°C.) | 110 | 110 | 100 |
| Final temperature (approx. °C.) | 140 | 140 | 150 |
| Pressure of flash evaporation (approx. mbar) | 95 | 48 | 50 |

The molar ratio of halogenobenzene to $HNO_3$ is in general from 0.9 to 1.5. In order to minimize the formation of unwanted dinitrohalogenobenzenes, the molar ratio of halogenobenzene to nitric acid is preferably from 1.0 to 1.5, particularly preferably from 1.01 to 1.3 and with very particular preference from 1.05 to 1.2. However, in the event that the nitrohalogenobenzenes obtainable in accordance with the invention are to be fed for dinitration, other ranges are also permissible, for example from 0.9 to 1.2 mol, preferably from 0.9 to 1.05 mol and particularly preferably from 0.95 to 1 mol of halogenobenzene per mole of nitric acid.

The reaction in the process according to the invention is expressed by the formula:

$$C_6H_5\text{---Hal} + HNO_3 \rightarrow O_2N\text{---}C_6H_4\text{---hal} + H_2O$$

Thus halogenobenzene and $HNO_3$ are introduced into the process and mononitrohalogenobenzene and $H_2O$ are expelled, while the $H_2SO_4/H_2O$ mixture described represents the reaction medium. Since dilute nitric acids are advantageously employed when the process is carried out industrially, it is also necessary, in addition to the water of reaction, to expel dilution $H_2O$ of the $HNO_3$.

The organic phase which is obtained on the separation of the reaction mixture can be worked up to give pure mononitrohalogenobenzene or can be fed to the dinitrohalogenobenzene preparation. In the former case at least molar quantities of halogenobenzene or a small molar excess will be employed, as described above, in order both to consume the $HNO_3$ and to suppress the second nitration; any excess of halogenobenzene is distilled off from the organic phase. The organic phase can be washed beforehand in order to separate off contaminants which are soluble in water, acid or alkali, such as inorganic and organic acids and phenolic contaminants. The formation of oxidation products (phenolic components, oxidation of the $CH_3$ group) is heavily suppressed. The formation of dinitrohalogenobenzenes is likewise heavily suppressed. However, these dinitrohalogenobenzenes do not constitute an interference if a second nitration is intended in any case; therefore, in such cases, a slightly substoichiometric amount of halogenobenzene may also be employed.

As a model for an industrial reactor which is free from back-mixing, and to represent the batchwise procedure, a batch formulation in a vigorously stirred, heat-insulated stirred flask, for example in a so-called sulphonation beaker, which is provided with baffles, can be used in the laboratory. In this case halogenobenzene, sulphuric acid and water are initially introduced at, for example, 110° C., and nitric acid which has been heated to the input temperature according to the invention and may be diluted by water and/or sulphuric acid is added in from 1 to 2 seconds. After the addition the reaction is allowed to proceed adiabatically. In this reaction the final temperature is reached in about 70 to 100 seconds (Examples 1 to 3). As an alternative it is also possible to introduce initially the total quantity of $HNO_3$, $H_2SO_4$ and $H_2O$ and to add the halogenobenzene to it; those skilled in the art will readily be able to recognize further addition variants. In this case the contents of the reaction vessel correspond, in the course of time, to one volume portion in axial motion through a tubular reactor with plug flow. That which occurs successively in time in the batch formulation proceeds in spatial succession in a tubular reactor, for example.

In this procedure for the process according to the invention in the laboratory, within the margins of analytical variation, a mixture of mononitrohalogenobenzenes is obtained which contains less than 0.01% of dinitrated compounds.

The yield of mononitrohalogenobenzenes, based on the nitric acid employed, is >95% of theory, in many cases >97%, and >98% for the continuous procedure.

After the reaction temperature has been achieved, the agitator is halted. The phases separate in approximately 20 seconds. A continuous industrial reactor is preferably dimensioned such that the reaction mixture reaches the final reaction temperature within the reactor.

The acid phase separated off after the reaction at the level of the respective final reaction temperature is colourless and clear and is concentrated in the manner described above, with the possible inclusion of the above-described extraction or reactive extraction. The circulating acid conducted in this way contains, after the process according to the invention, less than 25 ppm of nitric acid and less than 25 ppm of nitrous acid, for example from 5 to 20 ppm in each case, and possibly small quantities of organic impurities.

EXAMPLES

Example 1

41.3 g (0.367 mol) of chlorobenzene and 617.8 g of $H_2SO_4$ (72% strength) were introduced at 110° C. with stirring (1800 rpm; specific stirring power introduced: 22 W/l) into a heat-insulated sulphonation beaker (φ 100 mm) equipped with baffles and 2 turbine agitators (φ 39.9 mm) mounted on a shaft, and a mixture of 32.3 g (0.33 mol) of $HNO_3$ (65% strength) and 50 g of $H_2SO_4$ (72% strength), heated at 110° C., was added in from 1 to 2 sec. and the batch was reacted without cooling. After about 75 sec the reaction mixture had reached the final temperature of 134° C. and the agitator was halted. After phase separation (a few seconds) 77.2 g of organic phase were obtained.

| Composition (GC): | |
|---|---|
| chlorobenzene | 2.4% |
| 2-NCB | 58.2% |
| 3-NCB | 1.1% |
| 4-NCB | 38.4% |

(NCB = nitro-chlorobenzene)

3.8 g of organic components were obtained from the waste acid by extraction with methylene chloride.

| Composition (GC): | |
|---|---|
| chlorobenzene | 0% |

| Composition (GC): | |
|---|---|
| 2-NCB | 61.9% |
| 3-NCB | 0.6% |
| 4-NCB | 37.2% |
| Total yield | 95.1% of the theoretical yield |
| Ratio of p/o-NCB | 1.53. |

In this small batch the purpose of the extraction was for the complete determination of the yield; it is omitted in an industrial process.

Example 2

53.9 g (0.367 mol) of o-dichlorobenzene and 637.2 g of $H_2SO_4$ (78% strength) were introduced at 110° C. with stirring (1800 rpm; specific stirring power introduced: 22 W/l) into a heat-insulated sulphonation beaker as in Example 1, and a mixture of 32.3 g (0.333 mol) of $HNO_3$ (65% strength) and 50 g of $H_2SO_4$ (72% strength), heated at 110° C., was added in from 1 to 2 sec, and the batch was reacted without cooling. After about 95 sec the reaction mixture had reached the final temperature of 135° C. and the agitator was halted. After phase separation (a few seconds) 65.2 g of organic phase were obtained.

| Composition (GC): | |
|---|---|
| o-dichlorobenzene | 9.5% |
| 3,4-dichloronitrobenzene | 75.8% |
| 2,3-dichloronitrobenzene | 14.8% |

1.9 g of organic components were obtained from the waste acid by extraction with methylene chloride.

| Composition (GC): | |
|---|---|
| o-dichlorobenzene | 0.7% |
| 3,4-dichloronitrobenzene | 79.4% |
| 2,3-dichloronitrobenzene | 12.9% |
| Total yield | 96.0% of the theoretical yield. |

What is claimed is:

1. A process for the continuous preparation of a mononitrohalogenobenzene by reaction of a halogenobenzene with an $HNO_3/H_2SO_4/H_2O$ mixture with formation, essentially, of the mononitrohalogenobenzene and water of reaction, wherein the steps are a) feeding the reactants chlorobenzene or dichlorobenzene, and $HNO_3$, $H_2SO_4$ and $H_2O$ in any sequence into a reactor equipped with mixing elements, and which substantially prevents back-mixing of the reactants, a1) the quantity of $HNO_3$ is from 2.5 to 5% by weight, the quantity of $H_2SO_4$ is from 67.5 to 77% by weight and the quantity of $H_2O$ is the remainder to 100% by weight, and 100% by weight represents the sum of $HNO_3+H_2SO_4+H_2O$, a2) the $H_2O$ is employed as such, as dilution $H_2O$ of the $HNO_3$, as dilution $H_2O$ of the $H_2SO_4$ or in a plurality of the forms mentioned, and a3) the molar ratio of said chlorobenzene or dichlorobenzene to $HNO_3$ is from 1.05 to 1.2, b) rapid and intensive mixing of the total quantity of the reactants, at a temperature of 80° to 120° C. and with a mixing energy of from 3 to 30 watts per liter of the overall reaction mixture, c) carrying out the reaction under adiabatic conditions, d) separating the reaction mixture, after carrying out the reaction, into an organic and an inorganic phase, said inorganic phase having a sulphuric acid content of from 70 to 78% by weight, e) working up the substantially $HNO_3$-free inorganic phase by distillation with removal of water using the heat of reaction absorbed by the inorganic phase as a result of the adiabatic conditions in step c) as an energy source for the distillation, and f) recycling the distilled inorganic phase from step e) to step a) as a source of $H_2SO_4$ and $H_2O$.

2. The process of claim 1, wherein, in step b), a mixing energy is employed of from 3 to 30 watts per liter of the overall reaction mixture.

3. The process of claim 1, wherein the reactants are intensively mixed using mixing elements for a period of less than 3 sec before entry into the reactor which substantially prevents back-mixing, and are redispersed at least 2 times while flowing through the reactor.

4. The process of claim 1, wherein, in step e), the heat of reaction absorbed by the inorganic phase as a result of the adiabatic procedure is utilized for the distillative expulsion of water under a pressure of from 40 to 150 mbar.

5. The process of claim 4, wherein the distillative expulsion of water is carried out under a pressure of 40 to 120 mbar.

6. The process of claim 5, wherein the distillative expulsion of water is carried out under a pressure of 50 to 100 mbar.

7. The process of claim 4, wherein the temperature and concentration of the outflowing $H_2SO_4$ in the procedure of distillative expulsion of water are adjusted such that this outflowing $H_2SO_4$ is suitable directly for use in step a).

8. The process of claim 1, wherein the mixing is carried out in the range from 70° to 140° C.

9. The process of claim 8, wherein the mixing is carried out in the range from 80° to 120° C.

10. The process of claim 1, wherein the content of sulphuric acid in the inorganic phase after step d) is from 60 to 80% by weight.

11. The process of claim 10, wherein the content of sulphuric acid in the inorganic phase after step d) is from 68 to 80% by weight.

12. The process of claim 11, wherein the content of sulphuric acid in the inorganic phase after step d) is from 70 to 78% by weight.

13. The process of claim 1, wherein the content of added nitric acid in the reaction mixture at the time of mixing, relative to the sum of nitric acid, sulphuric acid and water, is from 2 to 6% by weight.

14. The process of claim 13, wherein the content of added nitric acid in the reaction mixture is from 2.5 to 5% by weight.

15. The process of claim 1, wherein the content of sulphuric acid in the reaction mixture at the time of mixing, relative to the sum of nitric acid, sulphuric acid and water, is from 65 to 79% by weight.

16. The process of claim 15, wherein the content of sulphuric acid in the reaction mixture is from 67.5 to 77% by weight.

17. The process of claim 1, wherein the molar ratio of halogenobenzene to nitric acid is from 1.0 to 1.5.

18. The process of claim 17, wherein the molar ratio of halogenobenzene to nitric acid is from 1.01 to 1.3.

19. The process of claim 18, wherein the molar ratio of halogenobenzene to nitric acid is from 1.05 to 1.2.

20. The process of claim 1, wherein the halogenobenzene is chlorobenzene or dichlorobenzene.

* * * * *

UNITED STATES PATENT AND TRADEMARK OFFICE
CERTIFICATE OF CORRECTION

PATENT NO. : 5,714,647
DATED : February 3, 1998
INVENTOR(S) : Blank, et al.

It is certified that error appears in the above-indentified patent and that said Letters Patent is hereby corrected as shown below:

Title Page [30] Foreign Application Priority Data:
Delete " 44 11 0064.2 " and substitute
-- 44 11 064.2 --

Signed and Sealed this

Second Day of June, 1998

Attest:

BRUCE LEHMAN

*Attesting Officer*  *Commissioner of Patents and Trademarks*